United States Patent
Ademe

(10) Patent No.: US 11,397,175 B2
(45) Date of Patent: Jul. 26, 2022

(54) METHOD AND APPARATUS FOR THE INSPECTION OF A PAPER WEB WOUND ON A BOBBIN

(71) Applicant: R.J. REYNOLDS TOBACCO COMPANY, Winston-Salem, NC (US)

(72) Inventor: Balager Ademe, Winston-Salem, NC (US)

(73) Assignee: RJ. Reynolds Tobacco Company, Winston-Salem, NC (US)

( * ) Notice: Subject to any disclaimer, the term of this patent is extended or adjusted under 35 U.S.C. 154(b) by 291 days.

(21) Appl. No.: 16/773,069

(22) Filed: Jan. 27, 2020

(65) Prior Publication Data

US 2021/0231635 A1    Jul. 29, 2021

(51) Int. Cl.

| | |
|---|---|
| *G01N 33/34* | (2006.01) |
| *B65H 18/10* | (2006.01) |
| *B65H 23/038* | (2006.01) |
| *G01N 13/00* | (2006.01) |
| *G01N 15/08* | (2006.01) |

(52) U.S. Cl.
CPC ......... *G01N 33/346* (2013.01); *B65H 18/103* (2013.01); *B65H 23/038* (2013.01); *G01N 13/00* (2013.01); *G01N 15/08* (2013.01); *G01N 15/082* (2013.01); *G01N 15/0806* (2013.01); *B65H 2801/54* (2013.01); *G01N 2013/003* (2013.01)

(58) Field of Classification Search
CPC ...... G01N 33/34; G01N 33/346; G01N 13/00; G01N 15/08; G01N 15/0806; G01N 15/082; B65H 2801/54; B65H 23/038; B65H 18/103
See application file for complete search history.

(56) References Cited

U.S. PATENT DOCUMENTS

| | | |
|---|---|---|
| 1,909,924 A | 5/1933 | Schweitzer |
| 1,996,002 A | 3/1935 | Seaman |
| (Continued) | | |

FOREIGN PATENT DOCUMENTS

| | | |
|---|---|---|
| EP | 0357359 A2 | 3/1990 |
| EP | 0486213 A1 | 5/1992 |
| (Continued) | | |

OTHER PUBLICATIONS

Eitzinger, "A Model for the Determination of Diffusion Capacity Under Non-Standard Temperature and Pressure Conditions", Beitrage zur Tabakforschung/Contributions to Tobacco Research, vol. 26 No. 2, Jul. 2014, pp. 50-56.

(Continued)

*Primary Examiner* — Nathaniel J Kolb
(74) *Attorney, Agent, or Firm* — Womble Bond Dickinson (US) LLP

(57) ABSTRACT

An apparatus adapted to examine a paper web includes a rotatable first bobbin, a rotatable second bobbin, and a first testing device. The first bobbin has a paper we wound thereabout that has transverse bands spaced apart along a length thereof. The second bobbin is arranged to receive the paper web from the first bobbin with a paper web path defined between the first and second bobbins. The first testing device is disposed along the paper web path and is arranged to nondestructively measure a diffusivity of one of the transverse bands of the paper web.

9 Claims, 4 Drawing Sheets

(56) References Cited

U.S. PATENT DOCUMENTS

| | | | |
|---|---|---|---|
| 1,999,223 A | 4/1935 | Weinberger |
| 1,999,224 A | 4/1935 | Miles |
| 2,013,508 A | 9/1935 | Seaman |
| 2,580,568 A | 1/1952 | Matthews |
| 2,754,207 A | 7/1956 | Schur |
| 2,755,207 A | 7/1956 | Frankenburg |
| 2,998,012 A | 8/1961 | Lamm |
| 3,030,963 A | 4/1962 | Cohn |
| 3,032,245 A | 5/1962 | George |
| 3,049,449 A | 8/1962 | Allegrini |
| 4,108,151 A | 8/1978 | Martin et al. |
| 4,146,040 A | 3/1979 | Cohn |
| 4,230,131 A | 10/1980 | Simon |
| 4,231,377 A | 11/1980 | Cline et al. |
| 4,246,775 A | 1/1981 | Stultz |
| 4,433,697 A | 2/1984 | Cline et al. |
| 4,450,847 A | 5/1984 | Owens |
| 4,452,259 A | 6/1984 | Norman et al. |
| 4,461,311 A | 7/1984 | Mathews et al. |
| 4,480,650 A | 11/1984 | Weinert |
| 4,489,738 A | 12/1984 | Simon |
| 4,607,647 A | 8/1986 | Dashley et al. |
| 4,615,345 A | 10/1986 | Durocher |
| 4,619,278 A | 10/1986 | Smeed et al. |
| 4,622,983 A | 11/1986 | Mathews et al. |
| 4,739,775 A | 4/1988 | Hampl, Jr. |
| 4,779,631 A | 10/1988 | Durocher et al. |
| 4,804,002 A | 2/1989 | Herron |
| 4,805,644 A | 2/1989 | Hampl, Jr. et al. |
| 4,845,374 A | 7/1989 | White et al. |
| 4,889,145 A | 12/1989 | Adams et al. |
| 4,915,118 A | 4/1990 | Kaufman et al. |
| 4,924,888 A | 5/1990 | Perfetti et al. |
| 4,941,485 A | 7/1990 | Perfetti et al. |
| 4,941,486 A | 7/1990 | Dube et al. |
| 4,998,541 A | 3/1991 | Perfetti et al. |
| 4,998,543 A | 3/1991 | Goodman et al. |
| 5,060,675 A | 10/1991 | Milford et al. |
| 5,092,306 A | 3/1992 | Bokelman et al. |
| 5,103,844 A | 4/1992 | Hayden et al. |
| 5,109,876 A | 5/1992 | Hayden et al. |
| 5,143,098 A | 9/1992 | Rogers et al. |
| 5,156,169 A | 10/1992 | Holmes et al. |
| 5,161,551 A | 11/1992 | Sanders et al. |
| 5,168,884 A | 12/1992 | Baldwin et al. |
| 5,191,906 A | 3/1993 | Myracle, Jr. |
| 5,220,930 A | 6/1993 | Gentry |
| 5,263,999 A | 11/1993 | Baldwin et al. |
| 5,271,419 A | 12/1993 | Arzonico et al. |
| 5,417,228 A | 5/1995 | Baldwin et al. |
| 5,450,863 A | 9/1995 | Collins et al. |
| 5,474,095 A | 12/1995 | Allen et al. |
| 5,699,811 A | 12/1997 | Paine, III |
| 5,849,153 A | 12/1998 | Ishino et al. |
| 5,878,753 A | 3/1999 | Peterson et al. |
| 5,878,754 A | 3/1999 | Peterson et al. |
| 5,927,288 A | 7/1999 | Bensalem et al. |
| 5,966,218 A | 10/1999 | Bokelman et al. |
| 5,979,461 A | 11/1999 | Bensalem et al. |
| 6,020,969 A | 2/2000 | Struckhoff et al. |
| 6,138,684 A | 10/2000 | Yamazaki et al. |
| 6,498,537 B1 | 12/2002 | Watanabe |
| 6,725,123 B1 * | 4/2004 | Denuell ............ G01N 21/89 |
| | | 250/548 |
| 2002/0092621 A1 | 7/2002 | Suzuki |
| 2003/0034042 A1 | 2/2003 | Kaneki et al. |
| 2003/0074954 A1 | 4/2003 | Engle et al. |
| 2003/0131860 A1 | 7/2003 | Ashcraft et al. |
| 2003/0145869 A1 | 8/2003 | Kitao et al. |
| 2003/0150466 A1 | 8/2003 | Kitao et al. |
| 2003/0164173 A1 | 9/2003 | Zawadzki et al. |
| 2003/0197126 A1 | 10/2003 | Sato et al. |
| 2004/0122547 A1 | 6/2004 | Seymour et al. |
| 2004/0187560 A1 | 9/2004 | Cholet |
| 2005/0044948 A1 * | 3/2005 | Belcastro ............ G01N 33/346 |
| | | 73/159 |
| 2005/0087202 A1 * | 4/2005 | Norman ............... G01N 13/00 |
| | | 131/908 |
| 2005/0115575 A1 * | 6/2005 | Seymour ............ A24C 5/3412 |
| | | 131/908 |

FOREIGN PATENT DOCUMENTS

| | | |
|---|---|---|
| EP | 1084629 A1 | 3/2001 |
| EP | 1084630 A1 | 3/2001 |
| EP | 1234514 A2 | 8/2002 |
| WO | 0108514 A1 | 2/2001 |
| WO | 0141590 A1 | 6/2001 |
| WO | 0148318 A1 | 7/2001 |
| WO | 0237991 A1 | 5/2002 |
| WO | 0243513 A1 | 6/2002 |
| WO | 0243514 A1 | 6/2002 |
| WO | 0244700 A1 | 6/2002 |
| WO | 02055294 A1 | 7/2002 |
| WO | 03019132 A1 | 3/2003 |
| WO | 03043450 A1 | 5/2003 |

OTHER PUBLICATIONS

Drake et al., "On a Cell to Measure Diffusion Coefficients of Gases Through Cigarette Papers", Int. J. Heat Mass Transfer, 1980, pp. 127-134, vol. 23.

International Search Report in the corresponding International Application No. PCT/IB2021/050598, dated Apr. 29, 2021.

* cited by examiner

METHOD AND APPARATUS FOR THE INSPECTION OF A PAPER WEB WOUND ON A BOBBIN

BACKGROUND

1. Technical Field

The present disclosure relates to smoking articles and, more particularly, to an apparatus for examining a length of a paper material suitable for use as a component of such a smoking article, in a nondestructive manner, whereafter the paper material can be used to manufacture the smoking article.

2. Discussion of Related Art

Smoking articles, such as cigarettes, have a substantially cylindrical rod shaped structure and include a charge, roll or column of smokable material such as shredded tobacco (e.g., in cut filler form) surrounded by a paper wrapper thereby forming a so-called "tobacco rod." Normally, a cigarette has a cylindrical filter element aligned in an end-to-end relationship with the tobacco rod. Typically, a filter element comprises plasticized cellulose acetate tow circumscribed by a paper material known as "plug wrap." Certain cigarettes incorporate a filter element having multiple segments, and one of those segments can comprise activated charcoal particles. Typically, the filter element is attached to one end of the tobacco rod using a circumscribing wrapping material known as "tipping paper." It may be desirable to perforate the tipping material and plug wrap in order to provide dilution of drawn mainstream smoke with ambient air. A cigarette is employed by a smoker by lighting one end thereof and burning the tobacco rod. The smoker then receives mainstream smoke into his/her mouth by drawing on the opposite end (e.g., the filter end) of the cigarette.

Numerous references propose various types of cigarettes possessing various types of paper wrapping materials. See, e.g., U.S Pat. No. 1,909,924 to Schweitzer; U.S Pat. No. 4,489,650 to Weinert; U.S Pat. No. 3,030,963 to Cohn; U.S. Pat. No. 4,146,040 to Cohn; U.S. Pat. No. 4,489,738 to Simon; U.S Pat. No. 4,615,345 to Durocher; U.S Pat. No. 4,607,647 to Dashley; U.S Pat. No. 5,060,675 to Milford et al.; U.S. Pat. No. 4,924,888 to Perfetti et al.; U.S Pat. No. 5,143,098 to Rogers et al.; U.S. Pat. No. 4,998,543 to Goodman; U.S Pat. No. 5,220,930 to Gentry; and U.S. Pat. No. 5,271,419 to Arzonico et al. Some paper wrapping materials are so-called "banded papers" and possess segments defined by the composition, location, and properties of the various materials within those wrapping materials. Numerous references contain disclosures suggesting various banded wrapping material configurations. See, e.g., U.S. Pat. No. 1,996,002 to Seaman; U.S Pat. No. 2,013,508 to Seaman; U.S. Pat. No. 4,452,259 to Norman et al.; U.S Pat. No. 5,417,228 to Baldwin et al.; U.S. Pat. No. 5,878,753 to Peterson et al., U.S. Pat. No. 5,878,754 to Peterson et al.; U.S. Pat. No. 6,198,537 to Bokelman et al.; U.S. Pat. No. 6,929,013 to Ashcraft et al.; and PCT WO 02/37991. Methods for manufacturing banded-type wrapping materials also have been proposed. See, e.g., U.S. Pat. No. 4,739,775 to Hampl, Jr.; U.S Pat. No. 5,474,095 to Allen et al.; PCT WO 02/44700; and PCT WO 02/055294. Some references further describe banded papers having segments of paper, fibrous cellulosic material, or particulate material adhered to a paper web. See, e.g., U.S. Pat. No. 5,191,906 to Myracle, Jr.; U.S. Pat. No. 5,263,999 to Baldwin et al.; U.S Pat. No. 5,417,228 to Baldwin et al.; U.S. Pat. No. 5,450,863 to Collins et al.; and U.S. Pat. No. 6,502,613 to Suzuki. In addition, some references describe apparatuses and method for inspecting such papers and wrapping materials, some of which may be capable of operating in an automated and/or high-speed process. See, e.g., U.S. Pat. No. 4,845,374 to White et al.; U.S Pat. No. 5,966,218 to Bokelman et al.; U.S Pat. No. 6,020,969 to Struckhoff et al.; U.S Pat. No. 6,198,537 to Bokelman et al.; U.S. Pat. Nos. 6,848,449 and 6,904,917 to Kitao et al.; U.S. Pat. No. 7,227,148 to Sato et al.; U.S Pat. No. 7,275,548 to Hancock et al.; and U.S. Patent Application Publication No. 2004/0231685.

Since certain properties are often required to provide the desired burn characteristics and/or other characteristics of such wrapping materials and since consistency between individual paper wrappers for a particular product may be desired, it may be desirable to determine certain physical properties or characteristics of wrapping materials for smoking articles. For example, techniques for measuring the air permeability or porosity of such wrapping papers, as well as the diffusion of gases, such as carbon monoxide, through such wrapping papers, have been developed. For example, the CORESTA method (CORESTA Publication ISO/TC0126/SC I Ni 59E (1986)) details a procedure for measuring air flow through paper with a specified pressure differential across the paper. Further, for example, Drake et al. (D. G. Drake, D. S. Riley, R. R. Baker and K. D. Kilburn, On a Cell to Measure Diffusion Coefficients of Gases Through Cigarette Papers, Int. J. Heat and Mass Transfer, 23 (1980) 127-134) describe a procedure for direct measurement of paper diffusion coefficients. In addition, U.S Pat. No. 4,615,345 to Durocher proposes an indirect and destructive sample test producing results asserted to be proportional to paper diffusion coefficients.

SUMMARY

There is a continuing need to verify certain physical properties of characteristics of paper webs of wrapping papers, such as those used for the manufacture of smoking articles, before the wrapping papers are used. It would also be desirable to expeditiously determine the particular characteristic of an entire bobbin of a paper web or a sample thereof and to have the capability to perform regular or random evaluations of the paper web in an automated fashion. Further, such an apparatus and method can be nondestructive to the paper web, applicable to a small area of the paper wrapper (sample), cost and time effective, and capable of being implemented in an environmentally friendly manner. Such an apparatus may be capable of advancing and retracting the paper web of the paper wrapper to identify a defective section of the paper web, which may be removed and/or further tested.

In various embodiments, the present disclosure provides an apparatus adapted to examine a paper web and a method of testing a paper web. The present disclosure includes, without limitation, the following example embodiments:

An apparatus adapted to examine a paper web, the apparatus comprising a rotatable first bobbin configured to accept a paper web, the paper web having transverse bands spaced apart along a length thereof, a rotatable second bobbin arranged to receive the paper web from the first bobbin with a paper web path defined between the first and second bobbins, and a first testing device disposed along the paper web path and arranged to nondestructively measure a diffusivity of one of the transverse bands of the paper web.

The apparatus of any preceding example embodiment, or any combination of any preceding example embodiments, further comprising a second testing device disposed along the paper web path and arranged to nondestructively measure a porosity of one of the transverse bands.

The apparatus of any preceding example embodiment, or any combination of any preceding example embodiments, wherein the second testing device is spaced apart along the paper web path from the first testing device by a distance corresponding to a distance between transverse bands of the paper web such that when one of the transverse bands is in registration with the first testing device another one of the transverse bands is in registration with the second testing device.

The apparatus of any preceding example embodiment, or any combination of any preceding example embodiments, further comprising a pattern detection device disposed along the paper web path prior to the first testing device and arranged to interact with the paper web to detect the transverse bands.

The apparatus of any preceding example embodiment, or any combination of any preceding example embodiments, wherein the pattern detection device is in communication with the first testing device and is arranged to provide a signal thereto when one of the detected transverse bands is in registration with the first testing device.

The apparatus of any preceding example embodiment, or any combination of any preceding example embodiments, wherein the pattern detection device is spaced apart along the paper web path from the first testing device by a distance corresponding to a distance between transverse bands of the paper web such that one of the transverse bands is in registration with the pattern detection device when another of the detected transverse bands is in registration with the first testing device.

The apparatus of any preceding example embodiment, or any combination of any preceding example embodiments, further comprising a drive system arranged to rotate the second bobbin to wind the paper web about the second bobbin as the paper web is unwound from the first bobbin.

The apparatus of any preceding example embodiment, or any combination of any preceding example embodiments, wherein the pattern detection device is in communication with the drive system and is arranged to provide a signal thereto to cease rotation of the second bobbin when one of the detected transverse bands is in registration with the first testing device.

The apparatus of any preceding example embodiment, or any combination of any preceding example embodiments, wherein the drive system is arranged to rotate the first bobbin to wind the paper web about the first bobbin as the paper web is unwound from the second bobbin.

The apparatus of any preceding example embodiment, or any combination of any preceding example embodiments, wherein the drive system includes a first motor arranged to rotate the first bobbin and a second motor arranged to rotate the second bobbin, wherein the first and second motors are reversible to reverse the progression of the paper web along the paper web path and to maintain a tension in the paper web.

The apparatus of any preceding example embodiment, or any combination of any preceding example embodiments, further comprising an optical imaging device disposed along the paper web path and arranged to capture an image of the one of the transverse bands.

An apparatus adapted to examine a paper web, the apparatus comprising a rotatable first bobbin configured to accept a paper web, the paper web having transverse bands spaced apart along a length thereof, a rotatable second bobbin arranged to receive the paper web from the first bobbin with a paper web path defined between the first and second bobbins, a first testing device disposed along the paper web path and arranged to nondestructively measure a property of one of the transverse bands of the paper web, and a drive system comprising a first motor arranged to rotate the first bobbin, and a second motor arranged to rotate the second bobbin, the first and second motors reversible to reverse the progression of the paper web along the paper web path and to maintain a tension in the paper web.

The apparatus of any preceding example embodiment, or any combination of any preceding example embodiments, wherein the first testing device is arranged to measure a diffusivity of one of the transverse bands of the paper web.

The apparatus of any preceding example embodiment, or any combination of any preceding example embodiments, further comprising a second testing device disposed along the paper web path and arranged to nondestructively measure a porosity of one of the transverse bands.

The apparatus of any preceding example embodiment, or any combination of any preceding example embodiments, wherein the second testing device is spaced apart along the paper web path from the first testing device by a distance corresponding to a distance between transverse bands of the paper web such that when one of the transverse bands is in registration with the first testing device another one of the transverse bands is in registration with the second testing device.

The apparatus of any preceding example embodiment, or any combination of any preceding example embodiments, further comprising a pattern detection device disposed along the paper web path prior to the first testing device and arranged to interact with the paper web to detect the transverse bands.

The apparatus of any preceding example embodiment, or any combination of any preceding example embodiments, wherein the pattern detection device is in communication with the first testing device and is arranged to provide a signal thereto when one of the detected transverse bands is in registration with the first testing device.

The apparatus of any preceding example embodiment, or any combination of any preceding example embodiments, wherein the pattern detection device is spaced apart along paper web path from the first testing device by a distance corresponding to a distance between transverse bands of the paper web such that one of the transverse bands is in registration with the pattern detection device when one of the detected transverse bands is in registration with the first testing device.

The apparatus of any preceding example embodiment, or any combination of any preceding example embodiments, wherein the pattern detection device is in communication with the drive system and is arranged to provide a signal thereto to cease rotation of the first and second bobbins when one of the detected transverse bands is in registration with the first testing device.

The apparatus of any preceding example embodiment, or any combination of any preceding example embodiments, further comprising an optical imaging device disposed along the paper web path and arranged to capture an image of the one of the transverse bands.

A method of testing a paper web, the method comprising advancing a paper web from a first bobbin to a second bobbin such that a band of the paper web is in registration with a first testing device positioned along a paper web path between the first and second bobbins, nondestructively measuring a diffusivity of the first band with the first testing device, and advancing the paper web to test a subsequent band when the diffusivity of the first band is within specification.

The method of any preceding example embodiment, or any combination of any preceding example embodiments, further comprising identifying the first band is out of specification, advancing the paper web such that a second band adjacent the first band is in registration with the first testing device, and nondestructively measuring a diffusivity of the second band with the first testing device.

The method of any preceding example embodiment, or any combination of any preceding example embodiments, further comprising retracting the paper web from the second bobbin to the first bobbin such that a third band adjacent the first band is in registration with the first testing device, the first band between the second and third bands, and nondestructively measuring a diffusivity of the third band with the first testing device.

The method of any preceding example embodiment, or any combination of any preceding example embodiments, further comprising identifying the first band as a singular error when the second and third bands are within specification.

The method of any preceding example embodiment, or any combination of any preceding example embodiments, further comprising identifying a defective section of the paper web when either the second band or the third band is outside of specification.

The method of any preceding example embodiment, or any combination of any preceding example embodiments, wherein identifying the defective section of the paper web comprises advancing the paper web such that a subsequent band beyond the second band is in registration with the first testing device, nondestructively measuring a diffusivity of the subsequent band with the first testing device, repeating advancing and nondestructively measuring a diffusivity of the subsequent bands until a subsequent band is within specification, and marking a first end of the defective section as the subsequent band within specification.

The method of any preceding example embodiment, or any combination of any preceding example embodiments, wherein repeating advancing and nondestructively measuring a diffusivity of subsequent bands includes increasing a length of advancement between subsequent bands when a subsequent band is out of specification.

The method of any preceding example embodiment, or any combination of any preceding example embodiments, wherein repeating advancing and nondestructively measuring includes advancing the paper web in a range of 2 centimeters to 10 meters between subsequent bands.

The method of any preceding example embodiment, or any combination of any preceding example embodiments, wherein identifying the defective section includes marking a second end of the defective section as a band previous to the first band which measured within specification.

The method of any preceding example embodiment, or any combination of any preceding example embodiments, further comprising marking a second end of the defective section, wherein marking the second end of the defective section comprises retracting the paper web such that a previous band beyond the third band is in registration with the first testing device, nondestructively measuring a diffusivity of the previous band with the first testing device, repeating retracting and nondestructively measuring a diffusivity of the previous bands until a previous band is within specification, and marking the second end of the defective section as the previous band within specification.

The method of any preceding example embodiment, or any combination of any preceding example embodiments, wherein advancing the paper web includes rotating the second bobbin with a first motor to wind the paper web about the second bobbin and to unwind the paper web from the first bobbin and applying tension to the paper web with a second motor engaged with the first bobbin, the second motor configured to rotate the first bobbin to wind the paper web about the first bobbin.

These and other features, aspects, and advantages of the disclosure will be apparent from a reading of the following detailed description together with the accompanying drawings, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification and the appended claims, the singular forms "a," "an," "the," and the like include plural referents unless the context clearly dictates otherwise. Also, while reference may be made herein to quantitative measures, values, geometric relationships, or the like, unless otherwise stated, any one or more if not all of these may be absolute or approximate to account for acceptable variations that may occur, such as those due to engineering tolerances or the like. As used herein, "substantially free" refers to concentrations of a given substance of less than 1% by weight or less than 0.5% by weight or less than 0.1% by weight based on total weight of a material.

Figure 1:
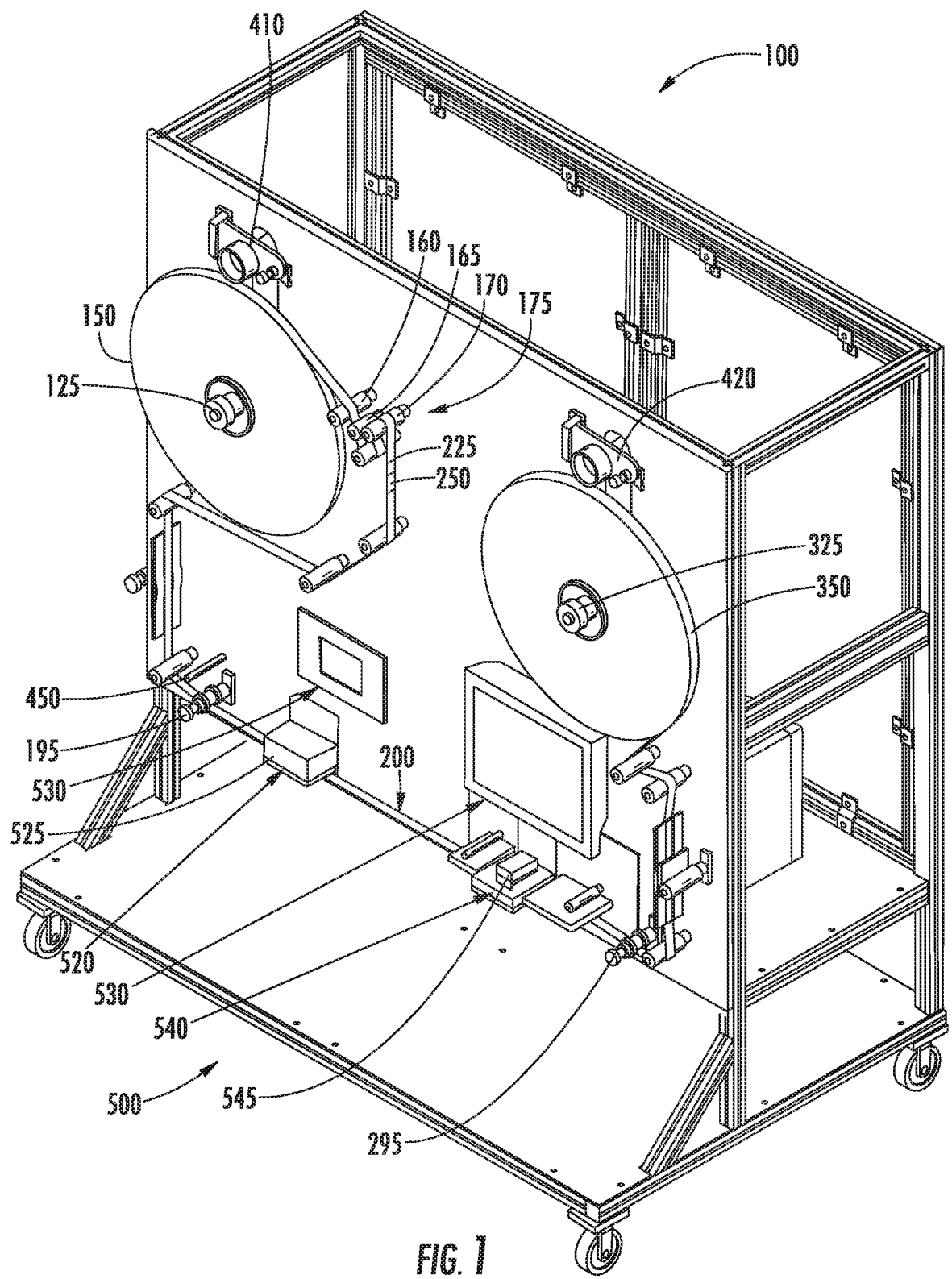
FIG. 1 is a front perspective view of an example cigarette paper testing apparatus provided in accordance with the present disclosure.
Figure 2:
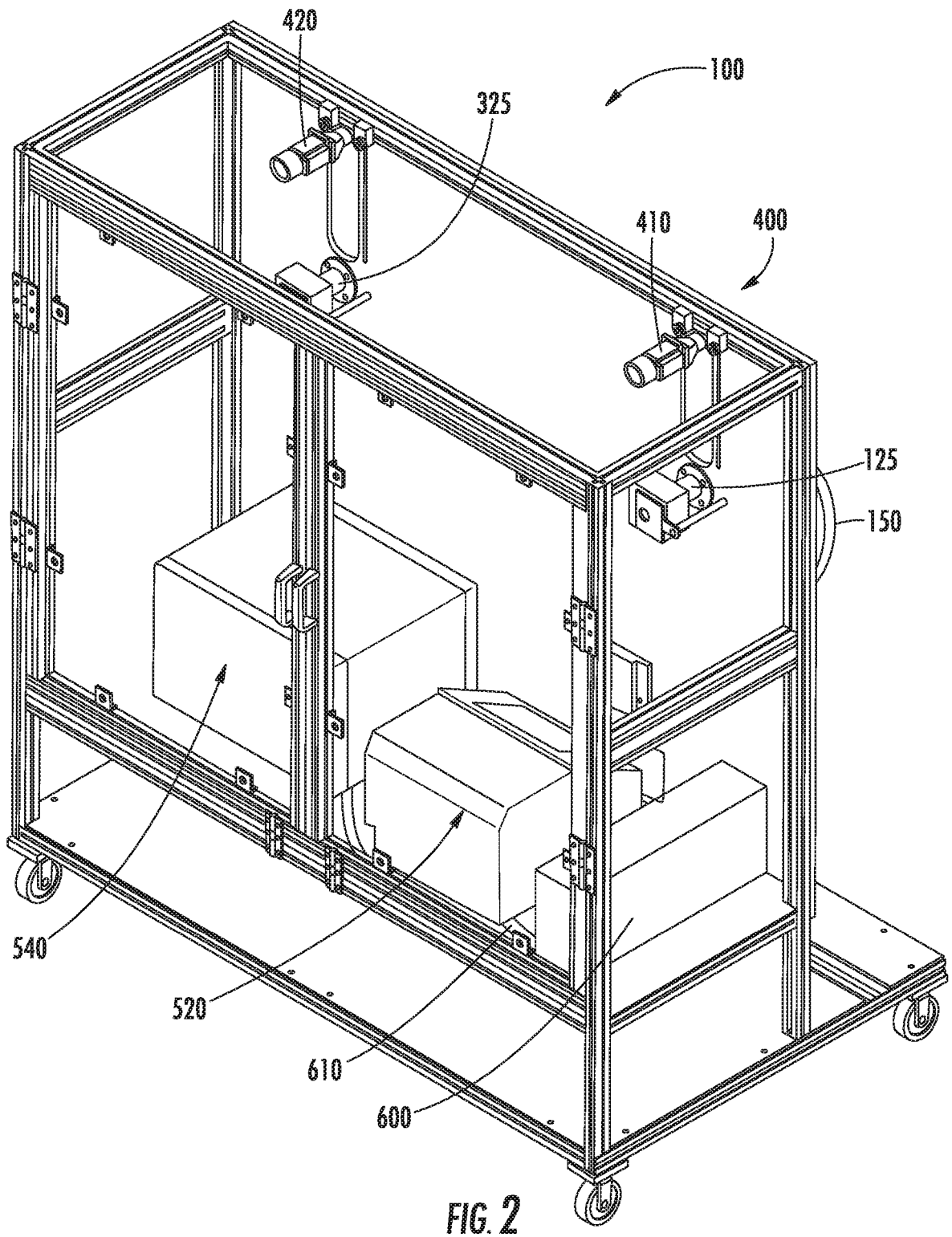
FIG. 2 is a rear perspective view of the apparatus of FIG. 1.

FIGS. 1 and 2 illustrate an example cigarette paper testing apparatus according to the present disclosure, the apparatus being indicated generally by the numeral 100. The apparatus 100 is configured to removeably receive a first bobbin 150 on a first spindle assembly 125. The first bobbin 150 having a continuous length of a wrapping material, such as a paper web 200 of a cigarette paper, wound thereon. The paper web 200 includes a selected pattern such as, for example, one or more bands (of which two bands 225, 250 are shown and described for illustrative purposes), wherein the bands 225, 250 may repeat along the length of the paper web 200. When the first bobbin 150 is engaged with the apparatus 100, the paper web 200 is routed along a path from the first bobbin 150 to a second bobbin 350 to be wound thereon. The second bobbin 350 is removeably mounted to a second spindle assembly 325.

The apparatus 100 of some example embodiments includes a drive system 400 that unwinds the paper web 200 from one of the first or second bobbins 150, 350 and winds the paper web 200 onto the other of the first or second bobbins 150, 350. The drive system 400 includes a first motor 410 associated with the first spindle 125 and/or first bobbin 150 and a second motor 420 associated with the second spindle 325 and/or second bobbin 350. For example, unwinding of the paper web 200 from the first bobbin 150 is drawn by the second motor 420 engaging the second bobbin 350 to rotate the second spindle 325 and the first motor 410 acting as a brake on the first bobbin 150 to create desired tension in the paper web 200. In addition, the paper web 200 may be wound onto the first bobbin 150 by the first motor 410 engaging the first bobbin 150 to rotate the first spindle 125 to draw the paper web 200 from the second bobbin 350 and to wind the paper web 200 about the first bobbin 150 with the second motor 420 acting as a brake on the second bobbin 350 to create desired tension in the paper web 200.

The apparatus 100 of some example embodiments includes a pattern (e.g., band) detection device 450 disposed between the first and second bobbins 150, 350. The pattern detection device 450 detects one or more of the bands along the length of the paper web 200. In the illustrated embodiments, a testing system 500 is disposed between the first and second bobbins 150, 350 and is configured to nondestructively determine one or more properties of the paper web 200, and specifically, properties of the bands 225, 250 of the paper web 200. The testing system 500 may include a first testing device 520 configured to determine a porosity of the paper web 200 and a second testing device 540 configured to determine a diffusivity of the paper web 200. Though the first and second testing devices 520, 540 are provided and described herein for illustrative purposes, one skilled in the art will appreciate that only one of those devices 520, 540 may be provided, or many other testing devices, in varying numbers, types, and/or combinations, may be provided and configured to nondestructively examine the paper web 200 between the first and second bobbins 150, 350. The drive system 400, the pattern detection device 450, and the first and second testing devices 520, 540 may be connected to communicate with a controller 600. In some instances, those components may be connected to communicate with the controller 600 through a control interface 610. Some embodiments may include one or more display panels 530. Examples of various techniques and equipment for handling, unwinding, and rewinding bobbins are set forth in U.S Pat. No. 4,619,278 to Smeed et al., U.S. Pat. No. 5,156,169 to Holmes et al., U.S. Pat. No. 5,966,218 to Bokelman et al., and U.S. Pat. No. 7,363,929 to Fagg et al.

Certain paper wrapping materials that may be examined by embodiments of the present disclosure are useful in the manufacture of cigarettes designed to exhibit reduced ignition propensity. That is, cigarettes incorporating certain wrapping materials, when placed on a flammable substrate, tend to self-extinguish before burning that substrate. Of particular interest are those cigarettes possessing tobacco rods manufactured using appropriate wrapping materials having bands comprised of appropriate amounts of suitable components to have the ability to meet certain cigarette extinction criteria.

The paper wrapping material that is further processed to provide the banded, or otherwise patterned, wrapping material can have a wide range of compositions and properties. The selection of a particular wrapping material will be readily apparent to those skilled in the art of cigarette design and manufacture. Typical paper wrapping materials are manufactured from fibrous materials, and optional filler materials, to form so-called "base sheets." Typical wrapping material base sheets suitable for use as the circumscribing wrappers of tobacco rods for cigarettes have basis weights that can vary. Typical dry basis weights of base sheets are at least 15 $g/m^2$, while typical dry basis weights do not exceed 80 $g/m^2$.

Typical wrapping material base sheets suitable for use as the circumscribing wrappers of tobacco rods for cigarettes have inherent porosities that can vary. Typical base sheets have inherent porosities that are at least 5 CORESTA units and less than 200 CORESTA units. A CORESTA unit is a measure of the linear air velocity that passes through a 1 $cm^2$ area of wrapping material at a constant pressure of 1 centibar. See CORESTA Publication ISO/TC0126/SC I N159E (1986). The term "inherent porosity" refers to the porosity of that wrapping material with respect to the flow of air. A particular paper wrapping material base sheet, for example, is comprised of wood pulp and calcium carbonate, and exhibits an inherent porosity of 20 to 50 CORESTA units.

Typical paper wrapping material base sheets suitable for use as the circumscribing wrappers of tobacco rods for cigarettes incorporate at least one type of fibrous material, and can incorporate at least one filler material, in amounts and type of material that can vary. Both components may affect the porosity and/or basis weight of the wrapping material. The fibrous material can be a cellulosic material, and the cellulosic material can be a lignocellulosic material. Example cellulosic materials include flax fibers, hardwood pulp, softwood pulp, hemp fibers, esparto fibers, kenaf fibers, jute fibers, and sisal fibers. Mixtures of two or more types of cellulosic materials can be employed. For example, wrapping materials can incorporate mixtures of flax fibers and wood pulp. The fibers can be bleached or unbleached. Other fibrous materials that can be incorporated within wrapping materials include microfibers materials and fibrous synthetic cellulosic materials. See, e.g., U.S Pat. No. 4,779,631 to Durocher and U.S Pat. No. 5,849,153 to Ishino. Representative fibrous materials, and methods for making wrapping materials therefrom, are set forth in U.S Pat. No. 2,754,207 to Schur et al.; and U.S. Pat. No. 5,474,095 to Allen et al.; and PCT WO 01/48318.

The wrapping material may also normally incorporate a filler material such as, for example, those set forth in PCT WO 03/043450. The filler material may have the form of essentially water insoluble particles and may normally incorporate inorganic components such as calcium salts or calcium carbonate, wherein calcium carbonate is typically used in particulate form. See, e.g., U.S Pat. No. 4,805,644 to Hampl; U.S. Pat. No. 5,161,551 to Sanders; and U.S Pat. No. 5,263,500 to Baldwin et al.; and PCT WO 01/48,316. Other filler materials include, for example, agglomerated calcium carbonate particles, calcium tartrate particles, magnesium oxide particles, magnesium hydroxide gels; magnesium carbonate-type materials, clays, diatomaceous earth materials, titanium dioxide particles, gamma alumina materials, and calcium sulfate particles. See, e.g., U.S Pat. No. 3,049,449 to Allegrini; U.S Pat. No. 4,108,151 to Martin; U.S. Pat. No. 4,231,377 to Cline; U.S Pat. No. 4,450,847 to Owens; U.S. Pat. No. 4,779,631 to Durocher; U.S Pat. No. 4,915,118 to Kaufman; U.S Pat. No. 5,092,306 to Bokelman; U.S Pat. No. 5,109,876 to Hayden; U.S Pat. No. 5,699,811 to Paine; U.S. Pat. No. 5,927,288 to Bensalem; U.S. Pat. No 5,979,461 to Bensalem; and U.S. Pat. No. 6,138,684 to Yamazaki; and European Patent Application 357359. Certain filler-type materials that can be incorporated into the wrapping materials can have fibrous forms, having components which may include materials such as glass fibers, ceramic fibers, carbon fibers and calcium sulfate fibers. See, e.g., U.S Pat. No. 2,998,012 to Lamm; U.S Pat. No. 4,433,679 to Cline; and U.S Pat. No. 5,103,844 to Hayden et al.; PCT WO 01/41590; and European Patent Application 1,084,629. Mixtures of filler materials can also be used.

There are various ways by which the various additive components can be added to, or otherwise incorporated into, the base sheet. Certain additives can be incorporated into the wrapping material as part of the paper manufacturing process associated with the production of that wrapping material. Alternatively, additives can be incorporated into the wrapping material using size press techniques, spraying techniques, printing techniques, or the like. Such techniques, known as "off-line" techniques, are used to apply additives to wrapping materials after those wrapping materials have been manufactured. Various additives can be added to, or otherwise incorporated into, the wrapping material simultaneously or at different stages during or after the paper manufacturing process.

The base sheets can be treated further, and those base sheets can be treated to impart a change to the overall physical characteristics thereof and/or to introduce a change in the overall chemical compositions thereof. For example, the base sheet can be electrostatically perforated as disclosed in U.S Pat. No. 4,924,888 to Perfetti et al. or embossed to provide texture to a surface thereof. Additives can be incorporated into the wrapping material, with representative additives, and methods for incorporating those additives to wrapping materials, being set forth in, e.g., U.S Pat. No. 5,220,930 to Gentry and U.S Pat. No. 5,168,884 to Baldwin et al. Certain components, such as alkali metal salts, can act as burn control additives and include, for example, alkali metal succinates, citrates, acetates, malates, carbonates, chlorides, tartrates, propionates, nitrates and glycolates; including sodium succinate, potassium succinate, sodium citrate, potassium citrate, sodium acetate, potassium acetate, sodium malate, potassium malate, sodium carbonate, potassium carbonate, sodium chloride, potassium chloride, sodium tartrate, potassium tartrate, sodium propionate, potassium propionate, sodium nitrate, potassium nitrate, sodium glycolate and potassium glycolate; and other salts such as monoammonium phosphate. Certain alkali earth metal salts also can be used. See, e.g., U.S. Pat. No. 2,580,568 to Matthews; U.S. Pat. No. 4,461,311 to Matthews; U.S. Pat. No. 4,622,983 to Matthews; U.S. Pat. No. 4,941,485 to Perfetti et al.; U.S Pat. No. 4,998,541 to Perfetti et al.; and PCT WO 01/08514. Certain components, such as metal citrates, can act as ash conditioners or ash sealers. See, e.g., European Patent Application 1,084,630.

Other representative components include organic and inorganic acids, such as malic, levulinic, boric and lactic acids (see, e.g., U.S Pat. No. 4,230,131 to Simon) or catalytic materials (see, e.g., U.S Pat. No. 2,755,207 to Frankenburg). Typically, the amount of chemical additive does not exceed 3 percent, based on the dry weight of the wrapping material to which the chemical additive is applied. For certain wrapping materials, the amount of certain additive salts, such as burn chemicals such as potassium citrate and monoammonium phosphate, for example in the range of 0.5 to 0.8 percent, based on the dry weight of the wrapping material to which those additive salts are applied. Relatively high levels of such additive salts can be used on certain types of wrapping materials printed with printed regions that are very effective at causing extinction of cigarettes manufactured from those wrapping materials.

Flavoring agents and/or flavor and aroma precursors (e.g., vanillin glucoside and/or ethyl vanillin glucoside) also can be incorporated into the paper wrapping material (see, e.g., U.S Pat. No. 4,804,002 to Herron and U.S Pat. No. 4,941,486 to Dube et al.) or printed onto cigarette papers. Some types of flavoring agents used in cigarette manufacture that are set forth in, for example, Gutcho, Tobacco Flavoring Substances and Methods, Noyes Data Corp. (1972) and Leffingwell et al., Tobacco Flavoring for Smoking Products (1972). Films can be applied to the paper (see, e.g., U.S Pat. No. 4,889,145 to Adams; U.S Pat. No. 5,060,675 to Milford et al., and PCT WO 02/43513 and PCT WO 02/055294), while catalytic materials can be incorporated into the paper. See, e.g., PCT WO 02/435134.

The composition of the additive material or coating formulation can vary, and is generally determined by the ingredients of the coating formulation. The coating formulation may have an overall composition, and be applied in a manner and in an amount, such that the physical integrity of the wrapping material is not adversely affected when the coating formulation is applied to selected regions of the wrapping material. In embodiments, the coating formulation may not introduce undesirable sensory characteristics to the smoke generated by a smoke article incorporating a wrapping material treated with that coating formulation. Suitable combinations of various components can act to reduce the effect of coatings on sensory characteristics of smoke generated by the smoking article during use. Some coatings also provide desirable physical characteristics to cigarettes manufactured from wrapping materials incorporating those coatings, and can be considered as adhesives since those coatings typically remain in contact with (e.g., to adhere to or otherwise remain secured to) desired locations on the wrapping material. Some examples of coating formulations and components thereof are set forth in U.S. Pat. No. 4,889,145 to Adams; and U.S Pat. No. 5,060,675 to Milford et al.; U.S. Pat. No. 6,848,449 to Kitao et al.; U.S Pat. No. 6,854,469 to Hancock et al.; U.S. Pat. No. 6,904,917 to Kitao et al.; U.S Pat. No. 6,929,013 to Ashcraft et al.; U.S. Pat. No. 7,363,929 to Fagg et al.; PCT WO 02/043513; PCT WO 02/055294; and European Patent Application 1,234,514.

The coating formulation may include a film-forming agent, such as a polymeric material or resin. Example film-forming agents include alginates (e.g., sodium alginate or ammonium alginate), pectins, derivatives of cellulose (e.g., carboxymethylcellulose and other polymeric materials such as hydroxypropylcellulose and hydroxyethylcellulose), ethylene vinyl acetate copolymers, guar gum, xanthan gum, starch (e.g., cornstarch, rice starch, and dextrin), modified starch (e.g., oxidized tapioca starch and oxidized corn starch), polyvinyl acetate, polyvinyl alcohol, and combinations thereof. Example blends include water-based blends of an ethylene vinyl acetate copolymer emulsion and polyvinyl alcohol, or water-based blends provided by mixing starches or modified starches with emulsion polymers or copolymers. The solvent or liquid carrier for the coating formulation can vary, and can be a liquid having an aqueous character, such as relatively pure water, or a non-aqueous solvent, such as ethanol, n-propyl alcohol, iso-propyl alcohol, ethyl acetate, n-propyl acetate, iso-propyl acetate, toluene, and the like.

The coating formulation also can include a filler material such as, for example, the essentially water insoluble types of filler materials previously described, may be in a finely divided (e.g., particulate) form. Typical fillers are those that have particle sizes that are less than 3 microns in diameter and suitably range from 0.3 micron to 2 microns in diameter. Example filler materials may comprise inorganic materials including metal particles and filings, calcium carbonate (e.g., precipitated-type fillers, including those having a prismatic form), calcium phosphate, clays (e.g., attapulgite clay), talc, aluminum oxide, mica, magnesium oxide, calcium sulfate, magnesium carbonate, magnesium hydroxide, aluminum oxide, and titanium dioxide. See, e.g., the types of filler materials set forth in U.S Pat. No. 5,878,753 to Peterson et al. Example filler materials also can be composed of organic materials including starches, modified starches and flours (e.g., rice flour), particles of polyvinyl alcohol, particles of tobacco (e.g., tobacco dust), fibrous cellulosic materials, and other like materials. See, e.g., U.S Pat. No. 5,417,228 to Baldwin et al. Alternate fillers can include carbon-based materials (e.g., graphite-type materials, carbon fiber materials and ceramics), metallic materials (e.g., particles of iron), and the like. The filler material also can be a water soluble salt (e.g., potassium chloride, sodium chloride, potassium citrate, sodium citrate, calcium chloride or magnesium chloride).

The coating formulations can incorporate other ingredients that may be dispersed or suspended therein to provide specific properties or characteristics to the wrapping material. Those ingredients can be, for example, preservatives (e.g., potassium sorbate), humectants (e.g., ethylene glycol and propylene glycol), pigments, dyes, colorants, burn promoters and enhancers, burn retardants and inhibitors, plasticers (e.g., dibutyl phthalate, polyethylene glycol, polypropylene glycol and triacetin), sizing agents, syrups (e.g., high fructose corn syrup), flavoring agents (e.g., ethyl vanillin and caryophyllene oxide), sugars (e.g., rhamnose), flavor precursors, hydrate materials, such as metal hydrates (e.g., borax, magnesium sulfate decahydrate, sodium silicate pentahydrate and sodium sulfate decahydrate), viscosity reducing agents (e.g., urea), and the like.

The amount of coating formulation that is applied to the paper wrapping material can vary, but typically provides a coated wrapping material having an overall dry basis weight (i.e., the basis weight of the whole wrapping material, including coated and uncoated regions) of at least 1.05 times that of the dry basis weight of that wrapping material prior to the application of coating thereto, and an overall dry basis weight of not more 1.4 times that of the dry basis weight of the wrapping material that has the coating applied thereto. Typical overall dry basis weights of those wrapping materials are between 20 g/m$^2$ to 40 g/m$^2$.

The dry weights of the coated regions of wrapping material of the present invention can vary. For wrapping materials that are used for the manufacture of cigarettes designed to meet certain cigarette extinction test criteria, it may be desirable that the wrapping materials have sufficient coating formulation applied thereto in the form of appropriately shaped and spaced bands in order that the dry weight of additive material applied to those wrapping materials totals at least 1 pound/ream, while the total dry weight of that applied additive material normally does not exceed 10 pounds/ream. As such, typical coated regions of paper wrapping materials suitable for use as the circumscribing wrappers of tobacco rods for cigarettes have inherent porosities that can vary. Typically, the inherent porosities of the coated regions of the wrapping materials are less than 8.5 CORESTA units, and at least 0.1 CORESTA unit. The inherent porosities of the coated regions of the wrapping materials, particularly those wrapping materials that are used for the manufacture of cigarettes designed to meet certain cigarette extinction test criteria, may be between 0.1 CORESTA unit and 4 CORESTA units.

Certain wrapping materials possess coatings in the form of patterns (e.g. bands) that extend across the wrapping material, generally perpendicular to the longitudinal axis of the wrapping material. The widths of the individual bands can vary, as well as the spacings between those bands. Typically, those bands have widths of between at least 0.5 mm and 8 mm. Such bands can be spaced apart such that the spacing between the bands is at least 10 mm, but usually no more than 50 mm.

Cigarettes designed to meet certain cigarette extinction test criteria can be produced from such wrapping materials, wherein the banded regions are produced using additive materials that are effective in reducing the inherent porosity of the wrapping material in those regions. Film-forming materials and fillers applied to the wrapping material in those banded regions are effective in increasing the weight of the wrapping material in those regions. Filler materials that are applied to the wrapping material in those banded regions are effective in decreasing the burn rate of the wrapping materials in those regions. Typically, when wrapping materials of relatively high inherent porosity are used to manufacture cigarettes, those wrapping materials possess relatively high weight bands that introduce a relatively low inherent porosity to the banded regions. Film-forming materials have a tendency to reduce the porosity of the wrapping material, whether or not those materials are used in conjunction with fillers. However, coatings that combine porosity reduction with added coating weight to wrapping materials also are effective in facilitating extinction of cigarettes manufactured from those wrapping materials. Low porosity in selected regions of a wrapping material tends to cause a lit cigarette to extinguish due to the decrease in access to oxygen for combustion for the smokable material within that wrapping material. Increased weight of the wrapping material also tends to cause lit cigarette incorporating that wrapping material to extinguish. As the inherent porosity of the wrapping material increases, it may also be desirable to select a film-forming material to cause a decrease the inherent porosity of the coated region of the wrapping material and/or provide a coating that provides a relatively large amount of added weight to the coated region of the wrapping material.

The diffusion of $CO_2$ through the wrapping material is known to affect the rate of burn of a smoking article manufactured with the wrapping material. Specifically, the higher the diffusion through the wrapping material, the faster the rate of burn and the lower the diffusion through the wrapping material, the slower the rate of burn. The diffusion through the wrapping material may differ for wrapping materials having identical air permeability. Thus, the diffusion of $CO_2$ may more precisely determine the rate of burn of a wrapping material than porosity measurements.

The diffusion and porosity effects resulting from treatment of the wrapping material base sheet are indicators of the characteristics of the smoking article produced therefrom. Accordingly, before such wrapping material is used to produce the smoking article, significant time and cost saving may be realized by first analyzing such factors of the wrapping material in order to determine that the characteristics of the wrapping material are within desired specifications and that the treatment of the wrapping material is consistent along the length of the wrapping material used in an automated cigarette manufacturing device.

Continuing the example of winding the paper web 200 from the first bobbin 150 to the second bobbin 350 and with reference to FIG. 1, as the paper web 200 is unwound from the first bobbin 150, the paper web 200 is directed around an arrangement of rollers (shown as rollers 160, 165, 170), otherwise referred to herein as a paper-engaging member or dancer assembly 175. The first motor 410 of some embodiments is configured to cooperate with the first bobbin 150 such that the first motor 410, in cooperation with the dancer assembly 175, takes up slack in the paper web 200 and maintains a desired tension on the paper web 200 as the paper web 200 is unwound from the first bobbin 150 and wound onto the second bobbin 350 by the drive system 400. The dancer assembly 175 may include a tensioner coupled to one of the rollers, e.g., roller 165, and configured to cooperate with the first motor 410 to provide the desired tension on the paper web 200.

The second motor 420 of some embodiments is operably engaged with the second bobbin 350 and configured to cooperate with the second bobbin 350 to wind the paper web 200 onto the second bobbin 350 while cooperating with the first bobbin 150, the first motor 410, and the dancer assembly 175 to maintain a desired tension in the paper web 200 between the first and second bobbins 150, 350. The paper web 200 may be supported, routed, and/or guided by any number of idler rollers, guideposts, air bars, turning bars, guides, tracks, tunnels, or the like for directing the paper web 200 along a desired path between the first and second bobbins 150, 350. The bobbins used during an automated cigarette making apparatuses often contain a continuous strip of the paper web 200 on the order of 6,500 meters in length, though the length of the paper web 200 may vary. As such, the apparatus 100 described herein is appropriately configured to handle bobbins of that type and size. The apparatus 100 may include tension rollers disposed the path between the first and second bobbins 150, 350 to provide a desired tension in the paper web 200 at different points in the path. In some embodiments, the apparatus 100 is provided without a dancer assembly, e.g., dancer assembly 175, with the motors 410, 420 exclusively taking up the slack and/or maintaining a desired tension in the paper web 200.

In the illustrated example, the strip of the paper web 200 extends past a first capstan 195 through the pattern detection device 450, the first testing device 520, and the second testing device 540 and into engagement with a second capstan 295 as the paper web 200 is advanced a first direction, e.g., from the first bobbin 150 to the second bobbin 350. In some embodiments, the first and second capstans 195, 295 may be configured to advance a small strip of the paper web 200 through the pattern detection device 450, the first testing device 520, and the second testing device 540 without utilizing the drive system 400 or the first and second bobbins 150, 350. Thus, a small strip of a paper web 200, e.g., 10 meters, may be tested instead of an entire bobbin. For additional reference to a suitable capstan drive system, reference may be made to U.S. Patent Application Publication No. 2005/0115575.

In some example embodiments where present, the first and second testing devices 520, 540, as well as the pattern detection device 450, are generally disposed between the first and second bobbins 150, 350. The pattern detection device 450 may be configured to detect at least one of the bands 225, 250 (or other pattern) of the paper web 200 as the paper web 200 is routed past the pattern detection device 450. The pattern detection device 450 may include an optical sensor configured to detect the bands 225, 250. One suitable optical sensor is manufactured by OMRON as a Model E3X-NL11 sensor and may include a Model ES32-S15-1 fiber optic element. Additionally or alternatively, the pattern detection device 450 may include a non-optical spectroscopic system, such as a non-contact ultrasonic transmission system or a near infrared (NIR) absorption system.

The first testing device 520 may include a testing head 525 configured to measure a porosity of a length of the paper web 200 positioned within the testing head 525 thereof. One suitable porosity sensor is manufactured by Borgwaldt as an A20 Air Permeability Tester. The second testing device 540 may include a testing head 545 configured to measure diffusivity of a length of the paper web 200 positioned within the testing head 545 thereof. The second testing device 540 may determine the paper diffusivity by measuring the gas diffusion capacity when $CO_2$ diffuses through the paper. One suitable diffusivity sensor is manufactured by SODIM SAS as SODISTAR.

The pattern detection device 450, the first testing device 520, and the second testing device 540 may be arranged in any order with one another. The pattern detection device 450 may be disposed in a known spaced relation with the first and/or second testing devices 520, 540 with respect to the path traveled by the paper web 200. In some embodiments, the pattern detection device 450, the first testing device 520, and/or the second testing device 540 may be movable with respect to each other along the path traveled by the paper web 200 such that the spacing between respective components is adjustable.

As described above, the length of the paper web 200 wound on the first bobbin 150 may include a pattern such as, for example, adjacent bands 225, 250, with the bands regularly repeating along the length of the paper web 200. The characteristics of such bands 225, 250 are generally determined by the treatment (or lack thereof) of the wrapping material base sheet in any of the manners previously described. Accordingly, for a band of particular interest to be tested along the length of the paper web 200, the distance between successive occurrences of that band (the band pitch) is determined and the appropriate distance is set between the pattern detection device 450 and each of the first and second testing devices 520, 540, and/or between the first and second testing devices 520, 540. This spacing may be set manually or, in some instances, may be entered into the controller 600, along with the desired measurement scheme, such that the testing parameters are automatically determined and set by the apparatus 100. In some instances, for example, the width of the paper web 200 may be 27 mm with a particular band extending for between 5 mm and 6 mm, and repeating at an interval of between 25 mm and 60 mm. In the alternative, the apparatus 100 may implement a search algorithm using any combination of the pattern detection device 450, the first and second testing devices 520, 540, and/or other components in order to locate the band or pattern of interest and determine the band pitch.

Both the first and second testing devices 520, 540 may be configured to test the same band or each testing device may be configured to test different bands. Further, the apparatus 100 may, in some instances, be configured to allow either of the testing devices 520, 540, or both, to examine the paper web 200 as the paper web 200 is advanced to the second bobbin 300 from the first bobbin 150. In some instances, the apparatus 100 may include multiples of each of the testing devices to allow similar measurements of different bands to occur concurrently.

The pattern detection device 450 is configured to detect the band or pattern of particular interest as the paper web 200 is advanced by the drive system. Accordingly, in order for the first and/or second testing devices 520, 540 to examine the paper web 200, the pattern detection device 450 of some example embodiments communicates with the drive system 400 through the controller 600 and/or the control interface 610, and cooperates therewith to stop the advancement of the paper web 200 when a particular band is detected and a measurement is to be made. In addition, the pattern detection device 450 of some such embodiments concurrently communicates with either or both of the first and second testing devices 520, 540 through the controller 600 and/or the control interface 610, and cooperates therewith to direct the appropriate testing device to perform the desired measurement on the paper web 200 once advancement of the paper web 200 is stopped. However, in some instances, the first or second testing devices 520, 540 may be configured to perform the appropriate examination of the paper web 200 without requiring the advancement of the paper web 200 to be stopped by the apparatus 100.

One skilled in the art will also appreciate that the measurements along the paper web 200 may occur in many different manners. For example, the apparatus 100 may be configured to measure every occurrence of a particular band or other pattern. In other instances, the apparatus 100 may be configured to perform the measurements at a particular interval along the length of the paper web 200, or at randomly selected points, to form a data profile of the paper web 200. In other instances, when considering the entire length of the strip of the paper web 200 (or an entire bobbin), the testing or sampling scheme may divide the paper web 200 into sections where, for example, the apparatus 100 may perform and average a certain number of measurements per section using parameters such as, for instance, distance between points in a section and distance between sections. Thus, the apparatus 100 may be configured to analyze the paper web 200 using many different measurement schemes. In any instance, the data collected by the first and/or second testing device(s) 520, 540, as well as other components of the apparatus 100, can be stored by the controller 600 or other storage device (not shown) for further analysis.

Once the paper web 200 has been examined by the first and/or second testing devices 520, 540 and determined to be acceptable or within specification, the second bobbin 300 can be removed from the apparatus 100 and stored as necessary. In some instances, the second bobbin 350 can be mounted onto a conventional type of automated cigarette making apparatus (not shown) in order to manufacture cigarettes using the examined paper web 200. In other instances, the apparatus 100 may also include an automatic bobbin changer device (not shown) configured to automatically move the second bobbin 350 to the automated cigarette making apparatus (not shown) once the desired length of the paper web 200 has been examined. If desired, the apparatus 100 can be operated to provide one examined second bobbin 350 at a time. Alternatively, the apparatus 100 can be adapted to provide an examined master roll or bobbin of the paper web 200, which then can be divided one or more times across the width of the roll to provide a plurality of bobbins, each of the desired width and having the desired length of the paper web 200 wound thereon. Alternatively, the apparatus 100 can be suitably adapted to simultaneously examine several strips or produce several examined second bobbins 350 at a time. The second bobbin 350 may be transferred to a cigarette manufacturing device and the paper web 200 subsequently used to produce cigarettes. In addition, the first and second bobbins 150, 350 may be interchangeable such that, once the first bobbin 150 is emptied by the apparatus 100, a new bobbin to be tested can be mounted to the second spindle 325 and unwound to the first bobbin 150 while being tested such that the first bobbin 150 essentially becomes a new second bobbin 350.

Alternatively, while the paper web 200 is examined by the first and/or second testing devices 520, 540 and an error is detected, e.g., an out of specification band or improper spacing between bands, the apparatus 100 may complete further testing and/or analysis on the paper web 200. When an error is identified, the controller 600 may perform an error algorithm to determine the extent of the error, the pattern of the error, the severity of the error, and/or a solution to the error.

Figure 3:
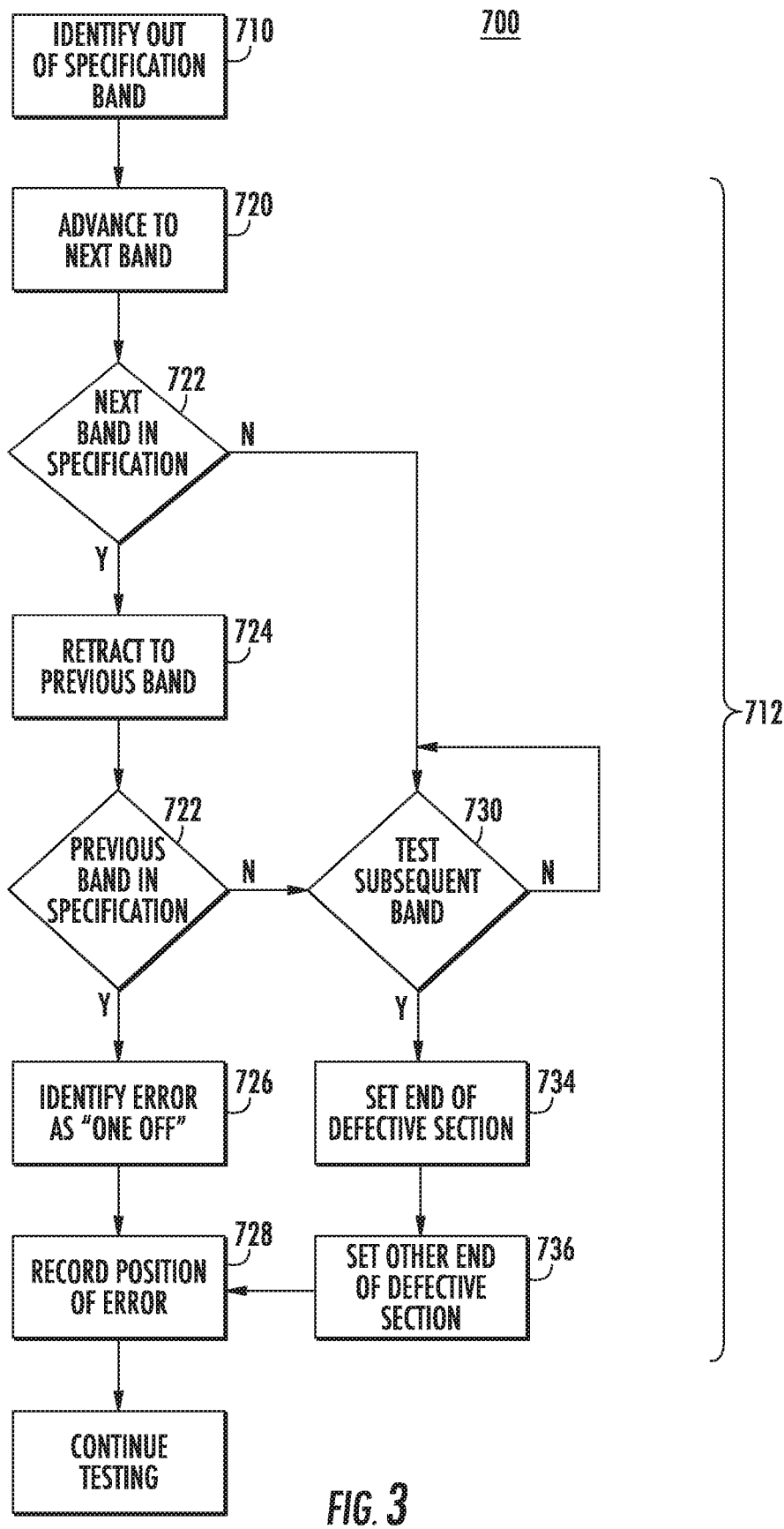
FIG. 3 is a flowchart of an embodiment of an error algorithm performed by a controller of the apparatus of FIG. 1 in accordance with the present disclosure.

Referring to FIG. 3, an example error algorithm 700 is disclosed with reference to the apparatus of FIGS. 1 and 2. Initially, during examination of the paper web 200, the error is identified in the controller 600 (Step 710). The error may be communicated to the controller 600 by the first or second testing device 520, 540 or the controller 600 may identify the error in data provided by the first or second testing device 520, 540.

When the error is identified, the controller 600 may determine a defective section of the paper web 200 by running a defect algorithm 712. To identify the defective section of the paper web 200, the controller 600 may advance the paper web 200 such that the next band is within the testing head 525, 545 of the respective testing device 520, 540 that generated the first error (Step 720). The next band is then tested and determined to be within specification or outside of specification (Step 722). If the next band is determined to be within specification, the controller 600 may reverse the paper web 200 such that the previous band, i.e., the band before the error was detected, is within the testing head 525, 545 of the respective testing device 520, 540 (Step 724). If the previous band is also determined to be within specification, the controller 600 identifies the error as a "one off" or singular error (Step 726) and returns to testing the remainder of the paper web 200. When the error is identified as a "one off" the apparatus 100 may include an optical imaging device, e.g., a camera (not shown), that captures an image of the band generating the first error. In addition, the controller 600 may record the position within the paper web 200 such that the band generating the first error may be removed before the paper web 200 is used in manufacturing, a product made with the band generating the first error can be discarded or tested, or to record the total number of bands generating errors within the paper web 200 (Step 728).

Alternatively, if either of the next or previous bands also fail to meet specification by generating an error, the controller 600 advances or retracts the paper web 200 to position and test a subsequent band beyond the next or previous band (Step 730). The subsequent band may be the adjacent the next or previous band or may be a predetermined number of bands beyond the next or previous band. For example, when the next band also generates an error, the controller 600 may advance the paper web 200 such that the subsequent band is in a range of 2 centimeters to 10 meters beyond the next band along a length of the paper web 200. If the subsequent band also generates an error, the controller 600 repeats positioning and testing subsequent bands until a subsequent band is determined to meet specification. The controller 600 may adjust the number of bands or length of paper web 20 between subsequent bands until a subsequent band is determined to meet specification. When a subsequent band is determined to meet specification, the controller 600 may reverse the direction of the paper web 200, e.g., begin retracting after advancing or begin advancing after retracting, until another band generates an error (Step 734). When another band generates an error, one end of the defective section is identified, e.g., the extent beyond the next band at which the error is no longer detected. The controller 600 may then identify the other end of the defective section of the paper web 200 by advancing or retracting in a similar manner from the first band generating the error (Step 736), e.g., the extent beyond the previous band at which the error is no longer detected. Alternatively, the controller 600 may determine the band that tested within specification prior to the first band generating the error to be the other end of the defective section of the paper web 200. With the ends of the defective section of the paper web 200 identified, the controller 600 may record the position within the paper web 200 such that the defective section may be removed before the paper web 200 is used in manufacturing, products made with the defective section of the paper web 200 can be discarded or tested, and/or to record the total number of bands within the defective section of the paper web 200 (Step 728).

In some embodiments, the error algorithm may include removing the defective section(s) of the paper web 200 such that the remainder of the paper web 200 may be sent to production. In some such embodiments, where multiple sections of non-defective paper web 200 remain after removing a defective section, the error algorithm may further include splicing two or more non-defective sections of the paper web 200 together. Removing defective section and splicing the paper web 200 may be completed by the apparatus or may be performed manually with the controller 600 positioning the ends of the defective section of the paper web 200 in predetermined positions to allow for removing of the defective section and splicing of the paper web 200. For example, the controller 600 may position one end of the defective section at the first capstan 195 and position the other end of the defective section at the second capstan 295. With the ends of the defective section positioned at each capstan 195, 295, the defective section may be removed and the ends of the remaining portions of the paper web 200 could be spliced together. Alternatively, one end of the defective section may be positioned at the second capstan 295 to allow for cutting of the paper web 200. The end of the defective section may then be wound onto separate spindle (not shown) and wound about the separate spindle until the other end of the defective section is positioned at the second capstan 295. The other end of the defective section is then cut at the remainder of the paper web 200 is spliced together with the defective section wound on the other bobbin.

Figure 4:
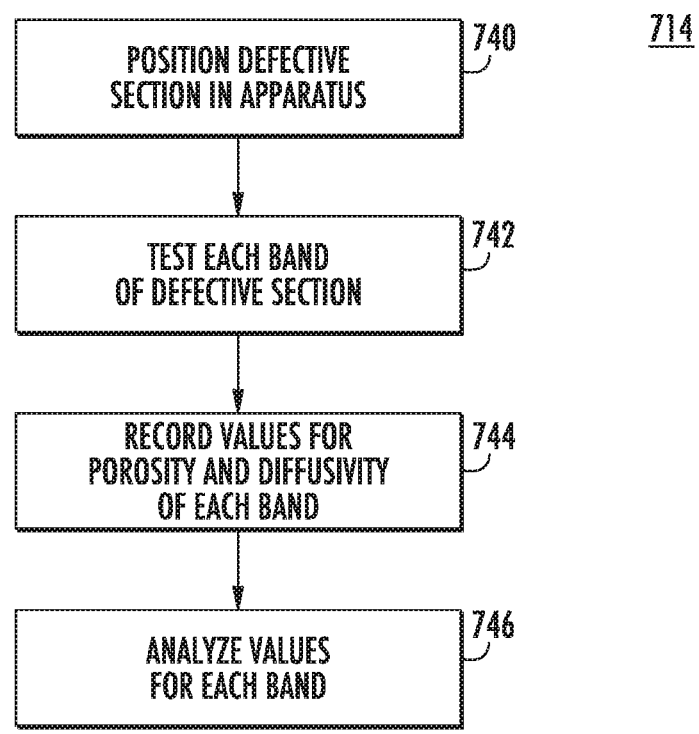
FIG. 4 is a flowchart of an embodiment of an error analysis algorithm that can be used in conjunction with the error algorithm of FIG. 3.

With reference to FIG. 4, with the defective section of the paper web 200 identified, the controller 600 may run an error analysis algorithm 714 to determine a pattern in the defective section of the paper web 200. Determining a pattern in the defective section may provide feedback to a manufacturer of the paper web 200 to improve manufacturing processes. Additionally or alternatively, the pattern in the defective section may be used to more quickly identify ends of future defective sections when a similar pattern or error is detected in another paper web. The error analysis algorithm 714 may be run with the defective section as part of the entire paper web 200 or the defective section may be removed from the paper web 200 and tested after the remainder of the paper web 200 is tested and processed. To run the error analysis algorithm 714, the defective section is positioned in the apparatus 100 such that each band of the defective section is tested by each of the first and second testing devices 520, 540 (Step 742). The values of porosity and diffusion are recorded for each band of the defective section (Step 744). The values of porosity and diffusion are then analyzed over the length of the defection section to determine a pattern (Step 746). In addition, the apparatus 100 may include an optical imaging device, e.g., a camera (not shown), that captures an image of the bands of the defective section. The values of porosity and diffusion for the bands of the defective section may be used to determine the root cause of the defective section and allow the manufacturer to take preventive measures to prevent future defects.

Many modifications and other embodiments of the inventions set forth herein will come to mind to one skilled in the art to which these inventions pertain having the benefit of the teachings presented in the foregoing descriptions and the associated drawings. For example, the apparatus 100 may also be configured to measure or otherwise determine that the appropriate amount of the paper web 200 is wound on either of the first and second bobbins 150, 350. In such instances, the apparatus 100 may also include components capable of allowing for automatic bobbin changing of the first bobbin 150 and splicing of the paper web 200, as well as an automatic rewind bobbin changer for changing the second bobbin 350 when the second bobbin 350 is full. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed:

1. A method of testing a paper web, the method comprising:
   advancing a paper web from a first bobbin to a second bobbin such that a band of the paper web is in registration with a first testing device positioned along a paper web path between the first and second bobbins;
   nondestructively measuring a diffusivity of the first band with the first testing device; and
   advancing the paper web to test a subsequent band when the diffusivity of the first band is within specification;
   identifying the first band is out of specification;
   advancing the paper web such that a second band adjacent the first band is in registration with the first testing device;
   nondestructively measuring a diffusivity of the second band with the first testing device;
   retracting the paper web from the second bobbin to the first bobbin such that a third band adjacent the first band is in registration with the first testing device, the first band between the second and third bands; and
   nondestructively measuring a diffusivity of the third band with the first testing device.

2. The method according to claim 1, further comprising identifying the first band as a singular error when the second and third bands are within specification.

3. The method according to claim 1, further comprising identifying a defective section of the paper web when either the second band or the third band is outside of specification.

4. The method according to claim 3, wherein identifying the defective section of the paper web comprises:
   advancing the paper web such that a subsequent band beyond the second band is in registration with the first testing device;
   nondestructively measuring a diffusivity of the subsequent band with the first testing device;
   repeating advancing and nondestructively measuring a diffusivity of the subsequent bands until a subsequent band is within specification; and
   marking a first end of the defective section as the subsequent band within specification.

5. The method according to claim 4, wherein repeating advancing and nondestructively measuring a diffusivity of subsequent bands includes increasing a length of advancement between subsequent bands when a subsequent band is out of specification.

6. The method according to claim 4, wherein repeating advancing and nondestructively measuring includes advancing the paper web in a range of 2 centimeters to 10 meters between subsequent bands.

7. The method according to claim 4, wherein identifying the defective section includes marking a second end of the defective section as a band previous to the first band which measured within specification.

8. The method according to claim 4, further comprising marking a second end of the defective section, wherein marking the second end of the defective section comprises:
   retracting the paper web such that a previous band beyond the third band is in registration with the first testing device;
   nondestructively measuring a diffusivity of the previous band with the first testing device;
   repeating retracting and nondestructively measuring a diffusivity of the previous bands until a previous band is within specification; and
   marking the second end of the defective section as the previous band within specification.

9. The method according to claim 1, wherein advancing the paper web includes rotating the second bobbin with a first motor to wind the paper web about the second bobbin and to unwind the paper web from the first bobbin and applying tension to the paper web with a second motor engaged with the first bobbin, the second motor configured to rotate the first bobbin to wind the paper web about the first bobbin.

* * * * *